US008183295B2

(12) United States Patent
Feldman et al.

(10) Patent No.: US 8,183,295 B2
(45) Date of Patent: May 22, 2012

(54) PHARMACEUTICAL COMPOSITION COMPRISING A RENIN INHIBITOR, A CALCIUM CHANNEL BLOCKER AND A DIURETIC

(75) Inventors: David L Feldman, Teaneck, NJ (US); Randy L Webb, Flemington, NJ (US)

(73) Assignee: Novartis Pharmaceuticals Corporation, East Hanover, NJ (US)

( * ) Notice: Subject to any disclaimer, the term of this patent is extended or adjusted under 35 U.S.C. 154(b) by 0 days.

(21) Appl. No.: 12/188,604

(22) Filed: Aug. 8, 2008

(65) Prior Publication Data

US 2008/0300238 A1 Dec. 4, 2008

Related U.S. Application Data

(63) Continuation of application No. 10/514,683, filed as application No. PCT/EP03/05188 on May 16, 2003, now abandoned.

(60) Provisional application No. 60/381,546, filed on May 17, 2002.

(51) Int. Cl.
*A61K 31/65* (2006.01)
*A61K 31/4418* (2006.01)
*A61K 31/4422* (2006.01)
*A61K 31/5415* (2006.01)

(52) U.S. Cl. ............... 514/620; 514/356; 514/223.2

(58) Field of Classification Search .................. None
See application file for complete search history.

(56) References Cited

U.S. PATENT DOCUMENTS

| 5,114,925 A | 5/1992 | Ashton et al. ............... 514/18 |
| 5,202,322 A | 4/1993 | Allen et al. ............... 514/228 |
| 5,656,650 A | 8/1997 | Weinstock ............... 514/396 |
| 5,948,799 A | 9/1999 | Cropp ............... 514/356 |
| 7,019,010 B2 | 3/2006 | Cohen ............... 514/263.34 |
| 2004/0242565 A1 | 12/2004 | Toshima et al. ............... 514/218 |

FOREIGN PATENT DOCUMENTS

| WO | WO 92/10097 | 6/1992 |
| WO | WO 02/40007 | 5/2002 |
| WO | WO 02/43807 | 6/2002 |

OTHER PUBLICATIONS

Low et al., Journal of Antimicrobial Chemotherapy, (1997), 39, Suppl. A, 53-58.*
Feldman et al, "Canadian recommendation for the management of hypertension", Canadian Medical Association Journal, 161 (12 Suppl), pp. S1-S8 (1999).
The Merck Manual, 17$^{th}$ edition, pp. 1635-1636 (1999).
Nussberger et al., Angiotensin II Suppression in Humans by the Orally Active Renin Inhibitor Aliskiren (SSP100), Hypertension 390;1-8 (2002).
Calhoun et al., Renin inhibitor aliskiren decreases plasma renin activity (PRA) Poster P 163 presented at ASH, New York, (May 20, 2008).
Wolters Kluwer Health, "Clinical Pharmacokinetics and Pharmacodynamics of aliskiren", Clinical Pharmacokinetics, 47 (8), pp. 515-531 (2008).
Drummond et al., "Antihypertensive efficacy of the oral direct renin inhibitor aliskiren as Add-On thereapy in patients not responding to amlodipine monotherapy", The Journal of Clinical Hypertension, vol. 9, No. 10 (Oct. 2007).

* cited by examiner

*Primary Examiner* — Phyllis G. Spivack
(74) *Attorney, Agent, or Firm* — Lisa Matovcik

(57) ABSTRACT

The invention relates to a pharmaceutical composition comprising (i) a renin inhibitor, (ii) a calcium channel blocker (CCB), and a diuretic and to a method of using such composition for the treatment of cardiovascular disease.

7 Claims, No Drawings

PHARMACEUTICAL COMPOSITION COMPRISING A RENIN INHIBITOR, A CALCIUM CHANNEL BLOCKER AND A DIURETIC

This application is a Continuation application of Ser. No. 10/514,683, filed Nov. 16, 2004, which is a 371 of PCT/EP03/05188, filed May 16, 2003, claiming benefit of Provisional Application 60/381,546, filed May 17, 2002.

The renin angiotensin system (RAS) is a complex hormonal system comprised of a large molecular weight precursor, angiotensinogen, two processing enzymes, renin and angiotensin converting enzyme (ACE), and the vasoactive mediator angiotensin II (Ang II) (J. Cardiovasc. Pharmacol., 15(Supp B) (1990) p. S1-S5). The enzyme renin catalyzes the cleavage of angiotensinogen into the decapeptide angiotensin I, which has minimal biological activity on its own and is converted into the active octapeptide Ang II by ACE. Ang II has multiple biological actions on the cardiovascular system, including vasoconstriction, activation of the sympathetic nervous system, stimulation of aldosterone production, antinatriuresis, stimulation of vascular growth (i.e., stimulation of smooth muscle cell proliferation and the deposition of excess extracellular matrix material in the vascular wall), and stimulation of cardiac growth. Ang II functions as a pressor hormone and is involved in the pathophysiology of several forms of hypertension.

The vasoconstrictive effects of angiotensin II are produced by its action on the non-striated smooth muscle cells, the stimulation of the formation of the adrenergenic hormones epinephrine and norepinephrine as well as the increase of the activity of the sympathetic nervous system as a result of the formation of norepinephrine. Angiotensin II also has an influence on electrolyte balance, produces e.g. antinatriuretic and antidiuretic effects in the kidney and thereby promotes the release of, on the one hand, the vasopressin peptide from the pituitary gland and, on the other hand, of aldosterone from the adrenal glomerulosa. All these influences play an important part in the regulation of blood pressure, in increasing both circulating volume and peripheral resistance. Angiotensin II is also involved in cell growth and migration and in extracellular matrix formation.

Angiotensin II interacts with specific receptors on the surface of the target cell. It has been possible to identify receptor subtypes that are termed e.g. AT1- and AT2-receptors. In recent times great efforts have been made to identify substances that bind to the AT1-the inhibition of the AT1-receptor such antagonists can be used e.g. as antihypertensives or for the treatment of congestive heart failure, among other indications. Angiotensin II antagonists are therefore understood to be those active ingredients that bind to the AT1-receptor subtype.

Inhibitors of the renin angiotensin system are well known drugs that lower blood pressure and exert beneficial actions in hypertension and in congestive heart failure as described, for example, in N. Eng. J. Med. 316, 23 (1987) p. 1429-1435. A large number of peptide and non-peptide inhibitors of the renin angiotensin system are known, the most widely studied being the ACE inhibitors, which include the drugs captopril, enalapril, lisinopril, benazepril and spirapril. Although a major mode of action of ACE inhibitors involves prevention of formation of the vasoconstrictor peptide Ang II, it has been reported in Hypertension, 16, 4 (1990) p. 363-370 that ACE cleaves a variety of peptide substrates, including the vasoactive peptides bradykinin and substance P. Prevention of the degradation of bradykinin by ACE inhibitors has been demonstrated, and the activity of the ACE inhibitors in some conditions has been reported in Circ. Res., 66, 1 (1990) p. 242-248 to be mediated by elevation of bradykinin levels rather than inhibition of Ang II formation. Consequently, it cannot be presumed that the effect of an ACE inhibitor is due solely to prevention of angiotensin formation and subsequent inhibition of the renin angiotensin system.

In addition to inhibiting the conversion of angiotensin I to angiotensin II, or blocking the AT1 receptor, the RAS can be stopped at the beginning of its pathway. This initial step (i.e., the conversion of angiotensinogen to angiotensin I) is mediated by renin and can be inhibited by renin inhibitors (RI). Renin inhibitors fully shut down the formation of angiotensin II because they act on the rate-limiting step in the cascade. Because of the virtually complete blockage of angiotensin II formation with RI, these agents can be demonstrated to have improved efficacy over ACE inhibitors or blockers of the AT1 receptor. Furthermore, because of their high degree of specificity, RI are associated with less side effects than ACE inhibitors. One such RI is aliskiren. Others are detikiren, terlakiren, and zankiren.

Aliskiren has the following chemical formula (I):

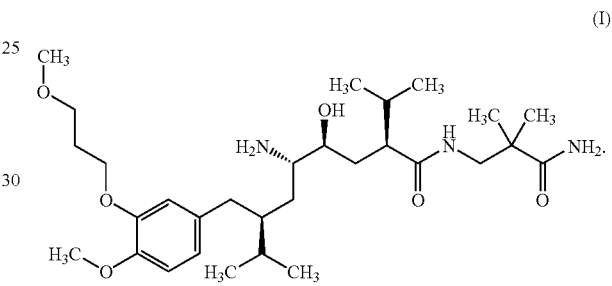

(I)

The renin inhibitor of formula (I), chemically defined as 2(S),4(S),5(S),7(S)—N-(3-amino-2,2-dimethyl-3-oxopropyl)-2,7-di(1-methylethyl)-4-hydroxy-5-amino-8-[4-methoxy-3-(3-methoxy-propoxy)phenyl]-octanamide, is specifically disclosed in EP 678503 A. Especially preferred is the hemi-fumarate salt thereof.

A drawback in the treatment of hypertension and diseases and conditions related thereto is that monotherapy frequently stimulates compensatory reflexes that counteract the pharmacologically-induced reduction in blood pressure. This compensation tends to hinder successful blood pressure lowering. It is therefore desirable to develop additional means of treatment for this application.

The present invention relates to a pharmaceutical composition comprising (i) a renin inhibitor, (ii) a calcium channel blocker (CCB), and (iii) a diuretic, or, where appropriate, in each case a pharmaceutically acceptable salt thereof, especially for the treatment of a disease or condition as set forth hereinbefore or hereinafter.

The invention likewise relates to the use of (i) a renin inhibitor, (ii) a calcium channel blocker (CCB), and (iii) a diuretic, or, where appropriate, in each case a pharmaceutically acceptable salt thereof, for the manufacture of a medicament for the treatment of a disease or condition as set forth hereinbefore or hereinafter.

The invention likewise relates to a method for the treatment of a disease or conditions as set forth hereinbefore or hereinafter comprising administering to an animal, including man, a therapeutically effective amount of (i) a renin inhibitor, (ii) a calcium channel blocker (CCB), and (iii) a diuretic, or, where appropriate, in each case a pharmaceutically acceptable salt thereof.

The present invention furthermore relates to a kit of parts comprising
(i) a pharmaceutical composition of a renin inhibitor or a pharmaceutically acceptable salt thereof, (ii) a pharmaceutical composition of a calcium channel blocker (CCB) or a pharmaceutically acceptable salt thereof, and (iii) a pharmaceutical composition of a diuretic, or a pharmaceutically acceptable salt thereof,
in the form of two or three separate units of the components (i) to (iii).

According to the invention the renin inhibitor (i) is selected from the group consisting of aliskiren, detikiren, terlakiren, and zankiren; (ii) the CCB is selected from the group consisting of amlodipine, felodipine, isradipine, lacidipine, nicardipine, nifedipine, niguldipine, niludipine, nimodipine, nisoldipine, nitrendipine, nivaldipine, ryosidine, anipamil, diltiazem, fendiline, flunarizine, gallopamil, mibefradil, prenylamine, tiapamil and verapamil; and the diuretic (iii) is selected from the group consisting of bumetanide, ethacrynic acid, furosemide, torsemide, amiloride, spironolactone, triamterene, chlorothalidone, chlorothiazide, hydrochlorothiazide, hydroflumthiazide, methylchlothiazide, metolazone, and dichlorphenamide and also amiloride. In each case where appropriate, e.g. if the compound is not present as a pharmaceutically acceptable salt per se as in the case of hydrochlorothiazide, these compounds also include their pharmaceutically acceptable salts.

The structure of the active agents identified by generic or tradenames may be taken from the actual edition of the standard compendium "The Merck Index" or from databases, e.g. LifeCycle Patents International (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

The present invention further relates to the above pharmaceutical composition for the treatment of heart failure such as (acute and chronic) congestive heart failure, left ventricular dysfunction and hypertrophic cardiomyopathy, diabetic cardiac myopathy, supraventricular and ventricular arrhythmias, atrial fibrillation, atrial flutter or detrimental vascular remodeling.

It can further be shown that combination therapy with the inventive combination and in particular with aliskiren, especially the hemi-fumarate salt thereof, amlodipine, especially the maleate or more preferably the besylate thereof, and hydrochlorothiazide (HCTZ) proves to be beneficial in the treatment and prevention of myocardial infarction and its sequelae. Such a combination therapy is also useful in treating atherosclerosis, angina (whether stable or unstable), and renal insufficiency (diabetic and non-diabetic). Furthermore, such a combination therapy can improve endothelial dysfunction, thereby providing benefit in diseases in which normal endothelial function is disrupted such as heart failure, angina pectoris and diabetes. Furthermore, the combination of the present invention may be used for the treatment or prevention of secondary aldosteronism, primary and secondary pulmonary hypertension, renal failure conditions, such as diabetic nephropathy, glomerulonephritis (including IgA nephropathy), renal fibrosis, scleroderma, glomerular sclerosis, proteinuria of renal disease, and also renal vascular hypertension, diabetic retinopathy, the management of other vascular disorders, such as migraine, peripheral vascular disease, Raynaud's disease, luminal hyperplasia, cognitive dysfunction (such as Alzheimer's), glaucoma and stroke, pulmonary and hepatic fibrosis, fibrotic diseases resulting from accumulation of excess extracellular matrix induced by TGF-β and proliferative diseases of smooth muscle cells (such as uterine fibroids).

The present invention furthermore relates to a method of treatment of a condition or a disease selected from the group consisting of hypertension, heart failure such as (acute and chronic) congestive heart failure, left ventricular dysfunction and hypertrophic cardiomyopathy, diabetic cardiac myopathy, supraventricular and ventricular arrhythmias, atrial fibrillation, atrial flutter, detrimental vascular remodeling, myocardial infarction and its sequelae, atherosclerosis, angina (whether unstable or stable), renal insufficiency (diabetic and non-diabetic), heart failure, angina pectoris, diabetes, secondary aldosteronism, primary and secondary pulmonary hypertension, renal failure conditions, such as diabetic nephropathy, glomerulonephritis (including IgA nephropathy), renal fibrosis, scleroderma, glomerular sclerosis, proteinuria of renal disease, and also renal vascular hypertension, diabetic retinopathy, the management of other vascular disorders, such as migraine, peripheral vascular disease, Raynaud's disease, luminal hyperplasia, cognitive dysfunction (such as Alzheimer's), glaucoma and stroke, pulmonary and hepatic fibrosis, fibrotic diseases resulting from accumulation of excess extracellular matrix induced by TGF, and proliferative diseases of smooth muscle cells, including uterine fibroids comprising administering a therapeutically effective amount of a combination of (i) a renin inhibitor, (ii) a CCB, and (iii) a diuretic, or pharmaceutically acceptable salts thereof and a pharmaceutically acceptable carrier to a mammal in need of such treatment. Preferably, the renin inhibitor is aliskiren, the CCB is amlodipine, and the diuretic is HCTZ.

The invention likewise relates to the use of a combination of (i) a renin inhibitor, (ii) a CCB, and (iii) a diuretic, or pharmaceutically acceptable salts for the treatment of a disease or condition as described hereinbefore or hereinafter.

As used throughout the specification and in the claims, the term "treatment" embraces all the different forms or modes of treatment as known to those of the pertinent art and in particular includes preventive, curative and palliative treatment.

Diuretic activates the RAS, thus makes inhibition of RAS by renin inhibitor (RI) more effective. Addition of CCB to RI, whose activity is potentiated by diuretic, will lower e.g. blood pressure by a mechanism separate from RAS. CCB has been shown to be renoprotective at least in part through (i) inhibition of glomerular expression of TGF-beta & alpha-smooth muscle cell actin (Nephron 2000 November; 86(3):315-26) and (ii) exerting growth-inhibitory activity through inhibiting multiple cell signal pathways (J Hypertens 2002 Jan.; 20(1): 95-102).

Surprisingly it was found that using the inventive combination of divergent mechanisms maximizes the chance to avoid the activation of compensatory blood pressure regulating mechanisms that are stimulated with mono-therapy antihypertensive treatment. Unexpectedly, blocking the RAS is most effective when the system is activated. Thus, it is possible to achieve greater pharmacological inhibition of the RAS when blockers of this system are administered simultaneously with mild activators of the RAS. Such activation of the RAS can be accomplished with the calcium channel blockers and diuretics. In addition, each of these therapies alone is antihypertensive. The use of an RI in this combination provides the most effective and complete blockage of the RAS. The unexpected advantage of a triple vs dual combination is the (i) potentiated blood pressure lowering effect and (ii) more effective anti-proliferative effect through the combined actions of rennin inhibition (potentiated by diuretic)

and CCB. Both of these activities are translated into enhanced tissue protection. The improved activity and benefit over dual combo results from a potentiation or even synergistic interactions between 3 components. Furthermore, less side effects are can be manifested by the ability to use lower doses of the partners to be combined. For example, doses of individual components can be reduced by 2-7 fold or reduced by 3-7, 4-7, 5-7 or 6-7 fold, when given in combination and still achieve comparable blood pressure lowering activity compared to each individual agent. In humans, the superiority or surprising advantages of triple over dual combos can be demonstrated e.g. by testing of the combination for benefits on blood pressure lowering, left ventricular hypertrophy, renal protection (e.g., reversing, ameliorating, or delaying worsening of proteinuria; slowing decline in glomerular filtration rate or creatinine clearance, delay doubling of serum creatinine).

Prolonged and uncontrolled hypertensive vascular disease ultimately leads to a variety of pathological changes in target organs such as the heart and kidney. The presence of diabetes exacerbates these changes. Sustained hypertension can lead as well to an increased occurrence of stroke. Therefore, there is a strong need to evaluate the efficacy of antihypertensive therapy, an examination of additional cardiovascular endpoints, beyond those of blood pressure lowering, to get further insight into the benefits of combined treatment. The nature of hypertensive vascular diseases is multifactorial. Under certain circumstances, drugs with different mechanisms of action have been combined. However, simply using any combination of drugs having different modes of action does not necessarily lead to combinations with advantageous effects.

Potentiation is the enhancement of the biological effect of one agent by another agent to produce either an additive or greater than additive biological effect, compared to the effects from the individual agents, while synergism is the enhancement of the biological effect of One agent by another agent to produce a biological effect that is greater than that predicted by adding the effects of the individual components.

In one aspect the present invention relates to a pharmaceutical composition comprising (i) aliskiren, (ii) amlodipine, and (ii) hydrochlorothiazide (HCTZ) or pharmaceutically effective salts thereof.

In another embodiment the present invention relates to methods of treating cardiac and renal related conditions by administration of the pharmaceutical composition comprising (i) aliskiren, especially the hemi-fumarate salt thereof, amlodipine, especially the maleate or more preferably the besylate thereof, and HCTZ.

The compounds to be combined can be present as pharmaceutically acceptable salts. If these compounds have, for example, at least one basic center, they can form acid addition salts. Corresponding acid addition salts can also be formed having, if desired, an additionally present basic center. The compounds having at least one acid group (for example COOH) can also form salts with bases. Corresponding internal salts may furthermore be formed, if a compound comprises e.g. both a carboxy and an amino group.

It has surprisingly been found that a combination of aliskiren, amlodipine, and HCTZ achieves greater therapeutic effect than the administration of each of these agents alone. Greater efficacy can also be documented as a prolonged duration of action. The duration of action can be monitored as either the time to return to baseline prior to the next dose or as the area under the curve (AUC) and is expressed as the product of the change in blood pressure in millimeters of mercury (change in mmHg) and the duration of the effect (minutes, hours or days).

Further benefits are that lower doses of the individual drugs to be combined according to the present invention can be used to reduce the dosage, for example, that the dosages need not only often be smaller but are also applied less frequently, or can be used to diminish the incidence of side effects. The combined administration of aliskiren, amlodipine, and HCTZ or pharmaceutically acceptable salts thereof results in a significant response in a greater percentage of treated patients, that is, a greater responder rate results, regardless of the underlying etiology of the condition. This is in accordance with the desires and requirements of the patients to be treated.

It can be shown that combination therapy with aliskiren, especially the hemi-fumarate salt thereof, amlodipine, especially the maleate or more preferably the besylate thereof, and HCTZ results in a more effective antihypertensive therapy (whether for malignant, essential, reno-vascular, diabetic, isolated systolic, or other secondary type of hypertension) through improved efficacy as well as a greater responder rate. The combination is also useful in the treatment or prevention of heart failure such as (acute and chronic) congestive heart failure, left ventricular dysfunction and hypertrophic cardiomyopathy, diabetic cardiac myopathy, supraventricular and ventricular arrhythmias, atrial fibrillation, atrial flutter or detrimental vascular remodeling. It can further be shown that combination therapy with aliskiren, amlodipine, and HCTZ proves to be beneficial in the treatment and prevention of myocardial infarction and its sequelae. A combination therapy with aliskiren, amlodipine, and HCTZ is also useful in treating atherosclerosis, angina (whether stable or unstable), and renal insufficiency (diabetic and non-diabetic). Furthermore, combination therapy using aliskiren, amlodipine, and HCTZ can improve endothelial dysfunction, thereby providing benefit in diseases in which normal endothelial function is disrupted such as heart failure, angina pectoris and diabetes. Furthermore, the combination of the present invention may be used for the treatment or prevention of secondary aldosteronism, primary and secondary pulmonary hypertension, renal failure conditions, such as diabetic nephropathy, glomerulonephritis (including IgA nephropathy), renal fibrosis, scleroderma, glomerular sclerosis, proteinuria of renal disease, and also renal vascular hypertension, diabetic retinopathy, the management of other vascular disorders, such as migraine, peripheral vascular disease, Raynaud's disease, luminal hyperplasia, cognitive dysfunction (such as Alzheimer's), glaucoma and stroke, pulmonary and hepatic fibrosis, fibrotic diseases resulting from accumulation of excess extracellular matrix induced by TGF-$\beta$ and proliferative diseases of smooth muscle cells (such as uterine fibroids).

The person skilled in the pertinent art is fully enabled to select a relevant test model to prove the efficacy of a combination of the present invention in the hereinbefore and hereinafter indicated therapeutic indications. Representative studies are carried out with a combination of aliskiren, especially the hemi-fumarate salt thereof, amlodipine, especially the maleate or more preferably the besylate thereof, and HCTZ applying the following methodology.

The advantages of the present combinations are, for example, demonstrated in a clinical study or in the test procedure as essentially described hereinafter. Many clinical study protocols adapted to test our combinations are known by the person skilled in the art. An example of a clinical trial useful to demonstrate the unexpected advantages of our new combinations is described by Nussberger J. et al. (Hypertension 2002 January; 39(1):E1-8). The same protocol is performed with our preferred combinations such as described herein. This protocol is hereby incorporated into the present application by reference to this publication.

Drug efficacy is assessed in various animal models including those found below, using the following approximate dosages. Aliskiren is administered in subcutaneously implanted osmotic minipumps at approximately 1-200 mg/kg/day (monotherapy), and approximately 1-75 mg/kg/day (combination therapy). Amlodipine and HCTZ are administered orally in dosages below 75 mg/kg/day as mono- or combination therapy.

Among the animal models used to assess drug efficacy are the deoxycorticosterone acetate-salt rat (DOCA-salt) and the spontaneously hypertensive rat (SHR) models, either maintained on a normal salt diet or with salt loading (4-8% salt in rat chow or 1% NaCl as drinking water). The DOCA-salt test model utilizes either an acute or chronic study protocol. An acute study procedure involves assessment of the effects of various test substances over a six-hour experimental period using rats with indwelling femoral arterial and venous catheters. The Acute Study Procedure evaluates test substances for their ability to reduce blood pressure during the established phase of DOCA-salt hypertension. In contrast, the Chronic Study Procedure assesses the ability of test substances to prevent or delay the rise in blood pressure during the development phase of DOCA-salt hypertension. Therefore, blood pressure will be monitored in the chronic study procedure by means of a radiotransmitter. The radiotransmitter is surgically implanted into the abdominal aorta of rats, prior to the initiation of DOCA-salt treatment and thus, prior to the induction of hypertension. Blood pressure is chronically monitored for periods of up 6 weeks (approximately one week prior to DOCA-salt administration and for 5 weeks thereafter).

Rats are anesthetized with 2-3% isoflurane in oxygen inhalant followed by Amytal sodium (amobarbital) 100 mg/kg, ip. The level of anesthesia is assessed by a steady rhythmic breathing pattern.

Acute Study Procedure:

Rats undergo a unilateral nephrectomy at the time of DOCA implantation. Hair is clipped on the left flank and the back of the neck and scrubbed with sterile alcohol swabs and povidone/iodine. During surgery rats are placed on a heating pad to maintain body temperature at 37 degrees C.

A 20 mm incision is made through the skin and underlying muscle to expose the left kidney. The kidney is freed of surrounding tissue, exteriorized and two ligatures (3-0 silk) are tied securely around the renal artery and vein proximal to their juncture with the aorta. The renal artery and vein are then severed and the kidney removed. The muscle and skin wounds are closed with 4-0 silk suture and stainless steel wound clips, respectively. At the same time, a 15 mm incision is made on the back of the neck and a 3-week-release pellet (Innovative Research of America, Sarasota, Fla.) containing deoxycorticosterone acetate (100 mg/kg) is implanted subcutaneously. The wound is then closed with stainless-steel clips and both wounds are treated with povidone/iodine; the rats are given a post-surgical intramuscular injection of procaine penicillin G (100,000 U) and buprenorphine (0.05-0.1 mg/kg) s.c. The rats are immediately placed on 1% NaCl+0.2% KCl drinking water; this treatment continues for at least 3 weeks at which time the animals have become hypertensive and available for experimentation.

Forty-eight hours prior to experimentation, animals are anesthetized with isoflurane and catheters are implanted in the femoral artery and vein for measuring arterial pressure, collection of blood, and administration of test compounds. Rats are allowed to recover for 48 hours while tethered in a Plexiglas home cage, which also serves as the experimental chamber.

Chronic Study Procedure:

This procedure is the same as above except that rats are implanted with a radiotransmitter, 7-10 days prior to the unilateral nephrectomy and initiation of DOCA and salt. In addition, rats do not undergo surgery for placement of femoral arterial and venous catheters. Radiotransmitters are implanted as described in M. K. Bazil, C. Krulan and R. L. Webb., Telemetric monitoring of cardiovascular parameters in conscious spontaneously hypertensive rats, J. Cardiovasc. Pharmacol. 22: 897-905, 1993.

Protocols are then set-up on the computer for measurement of blood pressure, heart rate, etc, at predetermined time points. Baseline data are collected at various time points and over various time intervals. For example, baseline or pre-dose values usually consist of data collection and averaging over 3 consecutive, 24-hour time periods prior to drug administration.

Blood pressure, heart rate and activity are determined at various pre-selected time points before, during, and after drug administration. All measurements are performed in unrestrained and undisturbed animals. The maximum study time, determined by battery life, could be as long as nine months.

Additionally, SHR are utilized to study the effects of aliskiren in combination with amlodipine and HCTZ The hypertensive background of the SHR is modified either by chronic salt loading in an effort to suppress the renin angiotensin system (RAS) or chronic salt depletion to activate the RAS in the SHR. These manipulations will be carried out to more extensively evaluate the efficacy of the various test substances. For experiments performed in spontaneously hypertensive rats (SHR), these animals are supplied by Taconic Farms, Germantown, N.Y. (Tac:N(SHR)fBR). A radiotelemetric device (Data Sciences International, Inc., St. Paul, Minn.) is implanted into the lower abdominal aorta of all test animals between the ages of 14 to 16 weeks of age. All SHR are allowed to recover from the surgical implantation procedure for at least 2 weeks prior to the initiation of the experiments. Cardiovascular parameters are continuously monitored via the radiotransmitter and transmitted to a receiver where the digitized signal is then collected and stored using a computerized data acquisition system. Blood pressure (mean arterial, systolic and diastolic pressure) and heart rate are monitored in conscious, freely moving and undisturbed SHR in their home cages. The arterial blood pressure and heart rate are measured every 10 minutes for 10 seconds and recorded. Data reported for each rat represent the mean values averaged over a 24 hour period and are made up of the 144-10 minute samples collected each day. The baseline values for blood pressure and heart rate consist of the average of three consecutive 24 hour readings taken prior to initiating the drug treatments. All rats are individually housed in a temperature and humidity controlled room and are maintained on a 12 hour light dark cycle.

In addition to the cardiovascular parameters, weekly determinations of body weight also are recorded in all rats. Treatments are administered in the drinking water, via daily oral gavage or in osmotic minipumps as stated above. If given in drinking water, water consumption is measured five times per week. Doses of drugs for individual rats are then calculated based on water consumption for each rat, the concentration of drug substance in the drinking water, and individual body weights. All drug solutions in the drinking water are made up fresh every three to four days.

Upon completion of the chronic studies, SHR or DOCA-salt rats are anesthetized and the heart rapidly removed. After separation and removal of the atrial appendages, left ventricle and left plus right ventricle (total) are weighed and recorded. Left ventricular and total ventricular mass are then normalized to body weight and reported. All values reported for blood pressure and cardiac mass represent the group mean±sem.

Vascular function and structure are evaluated after treatment to assess the beneficial effects of the combination. SHR are studied according to the methods described by Intengan H D, Thibault G, Li J S, Schiffrin E L, Circulation 1999, 100 (22): 2267-2275. Similarly, the methodology for assessing vascular function in DOCA-salt rats is described in Intengan H D, Park J B, Schiffrin, E L, Hypertension, 1999, 34(4 Part 2): 907-913.

Drug efficacy for inhibiting diabetic renal disease is assessed in various animal models including spontaneously diabetic (db/db) mice (Ziyadeh F, Hoffman B, Han D, Iglesias-de la Cruz M, Hong S, Isono M, Chen S, McGowan T, Sharma K. Long-term prevention of renal insufficiency, excess matrix gene expression, and glomerular mesangial matrix expansion by treatment with monoclonal antitransforming growth factor-β antibody in db/db diabetic mice. Proc Natl Acad Sci. 2000; 97:8015-8020). The db/db mouse is a widely used model for the renal glomerular lesions seen in non-insulin dependent diabetes (type 2 diabetes). Mice are treated daily with vehicle, monotherapy or combination therapy. Every 2 weeks throughout the study urine is collected to measure urinary albumin excretion. At the end of the experiment blood is collected for determining plasma creatinine levels. The kidneys are preserved in situ by perfusion fixation, they are removed and renal pathology is assessed quantitatively by light microscopy and image analysis. Drug efficacy is defined by the reduction (vs vehicle controls) of (i) urinary albumin exretion, (ii) plasma creatinine, and by (iii) the inhibition of renal glomerulosclerosis.

Drug efficacy for inhibiting renal fibrosis is assessed in various animal models including the unilateral ureter obstruction model in rats (Ishidoya, S; Morrissey, J; McCracken, R; Reyes, A; Klahr, S. Angiotensin II receptor antagonist ameliorates renal tubulointerstitial fibrosis caused by unilateral uretheral obstruction. Kid Int. 47:1285-1294, 1995). This model involves ligating one ureter, which results in renal fibrosis by 5 days in the kidney drained by that ureter. Drug efficacy is assessed by quantifying with light microscopy and image analysis, the extent of renal fibrosis among treated groups. ACE inhibitors and AT1 receptor blockers inhibit renal fibrosis in this model (Klar, S; Ishidoya, S; Morrissey, J. Role of angiotensin II in the tubulointerstitial fibrosis of obstructive nephropathy. Amer J Kid Dis. 26:141-146, 1995). It can therefore be demonstrated that combination therapy with aliskiren, amlodipine, and HCTZ provides increased protection vs monotherapy.

A therapeutically effective amount of each of the components of the combination of the present invention may be administered separately, simultaneously or sequentially and in any order. The unit dose form may also be a fixed combination.

The corresponding active ingredient or a pharmaceutically acceptable salt thereof may also be used in form of a hydrate or include other solvents used for crystallization. The pharmaceutical compositions according to the invention can be prepared in a manner known per se and are those suitable for enteral, such as oral or rectal, and parenteral administration to mammals (warm-blooded animals), including man, comprising a therapeutically effective amount of the pharmacologically active compound, alone or in combination with one or more pharmaceutically acceptable carriers, especially suitable for enteral or parenteral application. Typical oral formulations include tablets, capsules, syrups, elixirs and suspensions. Typical injectable formulations include solutions and suspensions.

The invention also relates to combining separate pharmaceutical compositions in kit form. That is a kit combining two or three separate units, e.g. an aliskiren pharmaceutical composition, an amlodipine pharmaceutical composition, and an HCTZ pharmaceutical composition, or in case of two separate units a kit combining a pharmaceutical composition of two of the active agents and a pharmaceutical composition of the remaining active ingredient. The kit form is particularly advantageous when the separate components must be administered in different dosage forms (e.g. parenteral aliskiren formulation and oral amlodipine and HCTZ formulations) or are administered at different dosage intervals.

In a preferred embodiment, the (commercial) product is a commercial package comprising as active ingredients the combination according to the present invention (in the form of two or three separate units of the components (i) to (iii)), together with instructions for its simultaneous, separate or sequential use, or any combination thereof, in the delay of progression or treatment of the diseases mentioned herein.

These pharmaceutical preparations are for enteral, such as oral, and also rectal or parenteral, administration to homeotherms, with the preparations comprising the pharmacological active compound either alone or together with customary pharmaceutical auxiliary substances. For example, the pharmaceutical preparations consist of from about 0.1% to 90%, preferably of from about 1% to about 80%, of the active compounds. Pharmaceutical preparations for enteral or parenteral administration are, for example, in unit dose forms, such as coated tablets, tablets, capsules or suppositories and also ampoules. These are prepared in a manner which is known per se, for example using conventional mixing, granulation, coating, solubilizing or lyophilizing processes. Thus, pharmaceutical preparations for oral use can be obtained by combining the active compounds with solid excipients, if desired granulating a mixture which has been obtained, and, if required or necessary, processing the mixture or granulate into tablets or coated tablet cores after having added suitable auxiliary substances.

The dosage of the active compound can depend on a variety of factors, such as mode of administration, homeothermic species, age and/or individual condition.

Preferred dosages for the active ingredients of the pharmaceutical combination according to the present invention are therapeutically effective dosages, especially those which are commercially available.

Aliskiren is supplied in the form of suitable dosage unit form, for example, a capsule or tablet, and comprising a therapeutically effective amount, e.g. from about 1 to about 1,000 mg, preferably from about 150 to about 500 mg, of aliskiren which may be applied to patients. Preferably, aliskiren is applied once a day.

In case of amlodipine, preferred dosage unit forms are, for example, tablets or capsules comprising e.g. from about 1 mg to about 40 mg, preferably 2.5 to 20 mg daily when administered orally. In case of HCTZ, preferred dosage unit forms are, for example, tablets or capsules comprising e.g. from about 5 mg to about 200 mg, preferably from about 5 mg to about 25 mg, administered orally once a day. The above doses encompass a therapeutically effective amount of the active ingredients of the present invention.

An example of a preferred composition comprises an amount of Aliskiren between 140 and 220 mg e.g. 160 mg, an amount of amlodipine between 2 and 12 mg (e.g. 2.5 or 5 or 10 mg) and an amount of HCTZ between 5 and 30 mg, preferably between 5 and 15 (e.g. 12.5 or 6.25 mg).

Another example of a preferred composition comprises an amount of Aliskiren between 350 and 550 mg e.g. 450 mg, an amount of amlodipine between 2 and 12 mg (e.g. 2.5 or 5 or 10 mg) and an amount of HCTZ between 5 and 30 mg preferably between 10 and 30 (e.g. 12.5 mg or 25 mg).

Another example of a preferred composition comprises an amount of Aliskiren between 550 and 700 mg e.g. 640 mg, an amount of amlodipine between 2 and 12 mg (e.g. 2.5 or 5 or 10 mg) and an amount of HCTZ between 5 and 30 mg preferably between 10 and 30 (e.g. 12.5 mg or 25 mg).

The invention claimed is:

1. A pharmaceutical composition consisting of
   (i) 150-500 mg aliskiren or a pharmaceutically acceptable salt thereof,
   (ii) 1.0-40 mg amlodipine or a pharmaceutically acceptable salt thereof,
   (iii) 5-200 mg hydrochlorothiazide, and one or more pharmaceutically acceptable carriers,
   wherein the amounts of (i) aliskiren or a pharmaceutically acceptable salt thereof, (ii) amlodipine or a pharmaceutically acceptable salt thereof and (iii) hydrochlorothiazide administered in combination achieve a greater therapeutic effect than the therapeutic effects achievable with the amounts of (i) aliskiren or a pharmaceutically acceptable salt thereof, (ii) amlodipine or a pharmaceutically acceptable salt thereof and (iii) hydrochlorothiazide administered alone.

2. A pharmaceutical composition according to claim 1, wherein the amount of amlodipine or a pharmaceutically acceptable salt thereof is from 2.5 to 25 mg.

3. A pharmaceutical composition according to claim 2, wherein the amount of hydrochlorothiazide is from 5 to 25 mg.

4. A pharmaceutical composition according to claim 1, wherein the amount of hydrochlorothiazide is from 5 to 25 mg.

5. A pharmaceutical composition consisting of:
   (i) 150-500 mg aliskiren or a pharmaceutically acceptable salt thereof,
   (ii) 1.0-40 mg amlodipine or a pharmaceutically acceptable salt thereof, and
   (iii) 5-200 mg hydrochlorothiazide, and one or more pharmaceutically acceptable carriers,
   wherein the amounts of (i) aliskiren or a pharmaceutically acceptable salt thereof, (ii) amlodipine or a pharmaceutically acceptable salt thereof and (iii) hydrochlorothiazide are administered in a unit dosage form, said combination achieving a greater therapeutic effect than the therapeutic effects achievable with the amounts of (i) aliskiren or a pharmaceutically acceptable salt thereof, (ii) amlodipine or a pharmaceutically acceptable salt thereof and (iii) hydrochlorothiazide administered alone.

6. A pharmaceutical composition consisting of:
   (i) 140-220 mg aliskiren or a pharmaceutically acceptable salt thereof,
   (ii) 2.0-12 mg amlodipine or a pharmaceutically acceptable salt thereof, and
   (iii) 5-15 mg hydrochlorothiazide, and one or more pharmaceutically acceptable carriers,
   wherein the amounts of (i) aliskiren or a pharmaceutically acceptable salt thereof, (ii) amlodipine or a pharmaceutically acceptable salt thereof and (iii) hydrochlorothiazide are administered in a unit dosage form, said combination achieving a greater therapeutic effect than the therapeutic effects achievable with the amounts of (i) aliskiren or a pharmaceutically acceptable salt thereof, (ii) amlodipine or a pharmaceutically acceptable salt thereof and (iii) hydrochlorothiazide administered alone.

7. A pharmaceutical composition consisting of:
   (i) 550-700 mg aliskiren or a pharmaceutically acceptable salt thereof,
   (ii) 2.0-12 mg amlodipine or a pharmaceutically acceptable salt thereof, and
   (iii) 5-30 mg hydrochlorothiazide, and one or more pharmaceutically acceptable carriers,
   wherein the amounts of (i) aliskiren or a pharmaceutically acceptable salt thereof, (ii) amlodipine or a pharmaceutically acceptable salt thereof and (iii) hydrochlorothiazide are administered in a unit dosage form, said combination achieving a greater therapeutic effect than the therapeutic effects achievable with the amounts of (i) aliskiren or a pharmaceutically acceptable salt thereof, (ii) amlodipine or a pharmaceutically acceptable salt thereof and (iii) hydrochlorothiazide administered alone.

* * * * *